(12) United States Patent
Tsubuku et al.

(10) Patent No.: US 9,596,746 B2
(45) Date of Patent: Mar. 14, 2017

(54) CHARGED PARTICLE BEAM GENERATOR, CHARGED PARTICLE IRRADIATION SYSTEM, METHOD FOR OPERATING CHARGED PARTICLE BEAM GENERATOR AND METHOD FOR OPERATING CHARGED PARTICLE IRRADIATION SYSTEM

(71) Applicant: Hitachi, Ltd., Tokyo (JP)

(72) Inventors: Kazunori Tsubuku, Tokyo (JP); Masumi Umezawa, Tokyo (JP); Takashi Iga, Tokyo (JP); Kouji Tobinaga, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/926,501

(22) Filed: Oct. 29, 2015

(65) Prior Publication Data
US 2016/0150630 A1 May 26, 2016

(30) Foreign Application Priority Data
Nov. 21, 2014 (JP) ................................. 2014-236712

(51) Int. Cl.
| | | |
|---|---|---|
| H05H 15/00 | (2006.01) | |
| H05H 7/00 | (2006.01) | |
| H05H 13/04 | (2006.01) | |
| H01J 37/317 | (2006.01) | |
| A61N 5/01 | (2006.01) | |

(Continued)

(52) U.S. Cl.
CPC ............... *H05H 7/001* (2013.01); *A61N 5/01* (2013.01); *A61N 5/1068* (2013.01); *H01J 37/3178* (2013.01); *H05H 7/08* (2013.01); *H05H 13/04* (2013.01); *A61N 2005/1087* (2013.01)

(58) Field of Classification Search
CPC ...... A61N 2005/1087; H01J 2237/0473; H01J 2237/0475
USPC ............................... 250/492.3; 315/503, 505
See application file for complete search history.

(56) References Cited

U.S. PATENT DOCUMENTS 7,102,144 B2 * 9/2006 Matsuda ................... A61N 5/10
250/492.1
7,122,811 B2 * 10/2006 Matsuda ................... A61N 5/10
250/492.3

(Continued)

FOREIGN PATENT DOCUMENTS

JP 5456562 B2 4/2014

*Primary Examiner* — Thuy Vinh Tran
(74) *Attorney, Agent, or Firm* — Mattingly & Malur, PC

(57) ABSTRACT

Provided are a charged particle beam generation apparatus, a charged particle beam irradiation apparatus, a particle beam therapy system, and a charged particle beam generation apparatus operating method capable of implementing injection of a charged particle beam into a circular accelerator at an arbitrary timing by setting a normal operation period of a linear accelerator to be larger than a shortest period and securing a stability of the beam. In timing control of controlling injecting, accelerating, emitting, and decelerating processes of a synchrotron (200), after an end of the emitting process, a linear accelerator (111) is allowed to stop repetition of an operation based on an after-end-of-emitting-process timing signal to be in a stand-by state and is allowed to be start the repetition of the operation in a constant period based on a master signal.

11 Claims, 10 Drawing Sheets

(51) Int. Cl.
*A61N 5/10* (2006.01)
*H05H 7/08* (2006.01)

(56) References Cited

U.S. PATENT DOCUMENTS

| | | | | |
|---|---|---|---|---|
| 7,227,161 B2 * | 6/2007 | Matsuda | .................. | A61N 5/10 250/492.1 |
| 7,425,717 B2 * | 9/2008 | Matsuda | .................. | A61N 5/10 250/492.3 |
| 7,560,717 B2 * | 7/2009 | Matsuda | .................. | A61N 5/10 250/288 |
| 7,576,342 B2 * | 8/2009 | Hiramoto | ................. | A61N 5/10 250/492.21 |
| 7,589,334 B2 * | 9/2009 | Hiramoto | ................. | A61N 5/10 250/492.1 |
| 7,709,818 B2 * | 5/2010 | Matsuda | ............. | A61N 5/1043 250/398 |
| 2011/0266981 A1 | 11/2011 | Umezawa et al. | | |

* cited by examiner

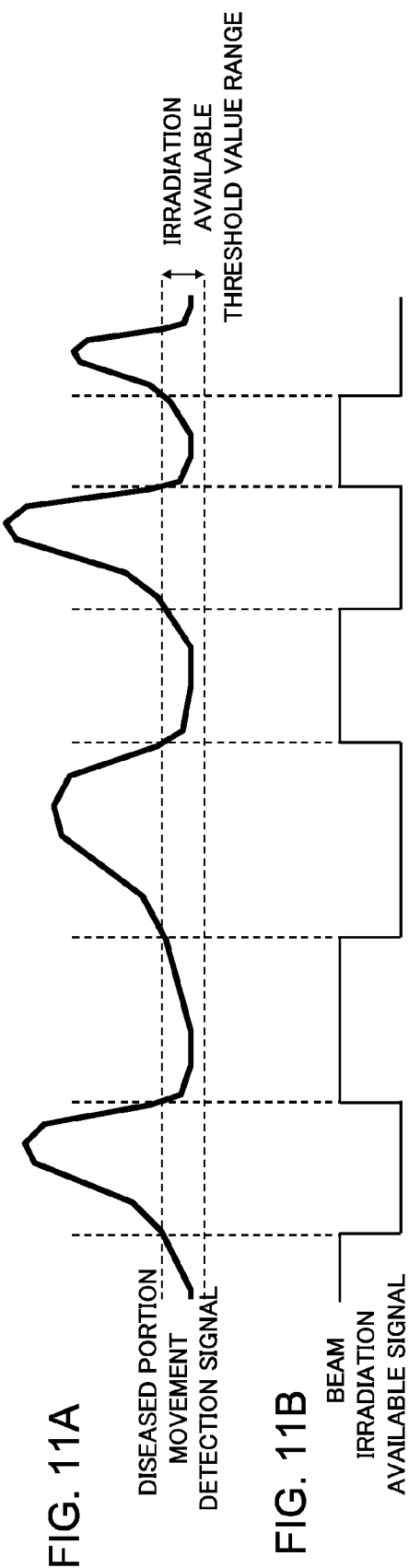

CHARGED PARTICLE BEAM GENERATOR, CHARGED PARTICLE IRRADIATION SYSTEM, METHOD FOR OPERATING CHARGED PARTICLE BEAM GENERATOR AND METHOD FOR OPERATING CHARGED PARTICLE IRRADIATION SYSTEM

TECHNICAL FIELD

The present invention relates to a charged particle beam generation apparatus, a charged particle beam irradiation apparatus, a particle beam therapy system, and a charged particle beam generation apparatus operating method.

BACKGROUND ART

In order to shorten an irradiation time interval and to reduce a treatment time interval by enabling injection of a charged particle beam into a circular accelerator at an arbitrary timing while maintaining a restriction of the shortest period of an operation period of a linear accelerator, PTL 1 discloses an invention where an accelerator control device controls an operation of a synchrotron by a beam emitting request signal from a beam utilization system control device and a control device generates a timing signal indicating an injection timing of a next operating cycle after an end of emission of the synchrotron and changes an operation timing transform of the linear accelerator to be coincident with the injection timing.

CITATION LIST

Patent Literature

PTL 1: Japanese Patent No. 5456562

SUMMARY OF INVENTION

Technical Problem

For a ring-shaped circular accelerator such as a synchrotron, a linear accelerator (LINAC) for accelerating and injecting charged particles is used in the front stage thereof. The linear accelerator accelerates the charged particles generated by an ion source up to predetermined energy and injects the accelerated charged particles into the circular accelerator. The particles accelerated up to higher energy by the circular accelerator are used for particle beam treatment of irradiating a diseased portion of a patient of a cancer or the like with the charged particle beam.

As an operation of the linear accelerator for injecting the charged particles into the circular accelerator for the particle beam treatment, there is known an operation of using high frequency voltage for acceleration, and a high frequency power supply device which generates the voltage is installed.

Therefore, the operation period of the linear accelerator is determined by an operation period of the high frequency power supply, and a minimum value of the period is, for example, 0.5 sec (frequency of 2 Hz), 0.2 sec (frequency of 5 Hz), or 0.33 sec (frequency of 30 Hz).

The reasons why the operation period of the linear accelerator is fixed or limited to the shortest period is as follows.

If the operation period of the high frequency power supply is set to be large, for example, if the operation period is set to be three or four times the fixed period or the shortest period, instability of the operation or the high frequency characteristics being deviated from a normal operation occurs, so that beam characteristics are affected.

In addition, if the period of the high frequency power supply is set to be small, for example, if the period is set to be as small as a fraction of 1 of the fixed period or the shortest period, thermal load or the like to the high frequency power supply or a high frequency device is increased, and thus, instability occurs, so that the beam characteristics are affected. In the case where the operation period is set to be small, with respect to the thermal load, the device may be out of order caused by heat thereof, and thus, in order to protect the device, an inter-operation time interval (operation period) needs to be taken to be long, in other words, the shortest period needs to be restricted. In addition, as the operation period is shortened, the life cycle of the device tends to be reduced.

On the other hand, in the case of the charged particle beam accelerated by the circular accelerator is used for the particle beam treatment, a position of the diseased portion may be changed according to the breathing or heart rate of the patient. The circular accelerator may be controlled to emit the charged particle beam only when the diseased portion is located at a predetermined position.

However, in the case where the injection into the circular accelerator intends to be performed at an arbitrary timing, since the operation period of the injector as a front-stage accelerator is restricted to a fixed or shortest period, a stand-by time corresponding to one operation period as the longest period from the injection-intending timing is required, and thus, a desired operation of the circular accelerator is impossible, and the irradiation time interval is increased by the stand-by time, so that the load to the patient is increased.

In addition, in the case where the charged particle beam is used for the particle beam treatment, there is a method of performing irradiating by dividing a diseased portion in a depth direction into layers, scanning an inner portion of the layer with a charged particle beam to be matched with a shape of the diseased portion, and changing energy of the charged particle beam emitted from a circular accelerator after an end of the irradiation of the inner portion of the layer.

In this irradiation, in the case of changing the layer of the irradiation object in the circular accelerator, a beam emission signal to a front-stage accelerator is transmitted to accelerate the charged particles. However, in the case where the operation period of the front-stage accelerator is restricted to a fixed or shortest period, a stand-by time corresponding to one operation period as the longest period from the injection-intending timing is required, and thus, a desired operation of the circular accelerator is impossible, and the irradiation time interval is increased by the stand-by time, so that the load to patient is increased.

In the linear accelerator for injection in the related art, since the operation period is restricted to be a fixed or shortest period as described above, the stand-by time corresponding to one operation period as the longest period with respect to the beam request timing from the circular accelerator is required. Therefore, in the case where a high-energy charged particle beam generated by the circular accelerator is used for the particle beam treatment, there is a problem in that, for the operation in synchronization with movement of the patient or for operation for the irradiation of a plurality of layers or areas obtained by dividing the diseased portion, the operation of the circular accelerator is restricted and the irradiation time interval for the patient is increased, and thus, the load to the patient is increased, so that the number of patients that can be treated per unit time in a treatment equipment is decreased.

On the other hand, in order to enable utilizing the beam at an arbitrary timing in the linear accelerator for injection, the operation period needs to be changeable, particularly, the inter-operation time interval, namely, the operation time of the high frequency power supply needs to be shortened. However, there is a problem in that, due to the influence, instability is expected to occur in the operation of the linear accelerator or the beam characteristics, or the device is expected not to be normally operated due to the thermal load or the like to the high frequency power supply or the high frequency device, and as the measures, the high frequency power supply needs to be configured with high performance and the linear accelerator needs to be configured with a large size.

Furthermore, in the technique disclosed in PTL 1, in the case where the operation period of the linear accelerator is longer than a time interval from the generation of the timing signal indicating the injection timing of the next operating cycle to the injection, the synchrotron side waits for the injection timing while maintaining an original injector high frequency operation timing. Therefore, if the operation period of the linear accelerator is set to be as short as possible, for example, the following situation may frequently occur. There is a problem in that, the timing signal indicating the injection timing of the next operating cycle immediately follows the pervious-time pulse in the operation period of the linear accelerator, before the next pulse in the operation period of the linear accelerator after re-sampling arrives, a beam request (beam request of the synchrotron) arrives, and thus, beam supply is not coincident with a timing, so that a stand-by time occurs.

The present invention is to provide a charged particle beam generation apparatus, a charged particle beam irradiation apparatus, a particle beam therapy system, and a charged particle beam generation apparatus operating method capable of implementing injection of a charged particle beam into a circular accelerator at an arbitrary timing by setting a normal operation period of a linear accelerator to be larger than a shortest period and securing a stability of the beam.

Solution to Problem

In order to solve the aforementioned problems, for example, configurations disclosed in Claims are employed.

According to an aspect the present, there is provided a charged particle beam generation apparatus including a linear accelerator which is operated in a predetermined operation period and accelerates charged particles emitted from an ion source to emit a charged particle beam, a ring-shaped circular accelerator which is operated in an operation period including time intervals of injecting, accelerating, emitting, and decelerating processes for the charged particle beam, injects the charged particle beam accelerated by the linear accelerator in a predefined timing and accelerates the charged particle beam to emit the charged particle beam, and a control device which, after an end of the charged particle beam emitting process in the operation period of the circular accelerator, generates an after-end-of-emitting-process timing signal, stops the linear accelerator based on the after-end-of-emitting-process timing signal, generates a synchrotron pattern start signal indicating a next operation start timing, and starts an operation in a predetermined operation period of the linear accelerator and an operation of the linear accelerator based on the synchrotron pattern start signal.

Advantageous Effects of Invention

According to the present invention, injection of a charged particle beam of a linear accelerator into a circular accelerator can be performed at an arbitrary timing, and thus, the beam is stabilized, so that it is possible to elongate a life cycle of a device, to shorten an irradiation time interval, or to reduce a treatment time interval.

BRIEF DESCRIPTION OF DRAWINGS

FIGS. 11A and 11B are diagrams illustrating a relation between a diseased portion movement detection signal and a beam irradiation available signal in the charged particle beam irradiation apparatus according to the third embodiment of the present invention.

DESCRIPTION OF EMBODIMENTS

Hereinafter, preferred embodiments of the present invention will be described with reference to the drawings.

First Embodiment

Figure 1:
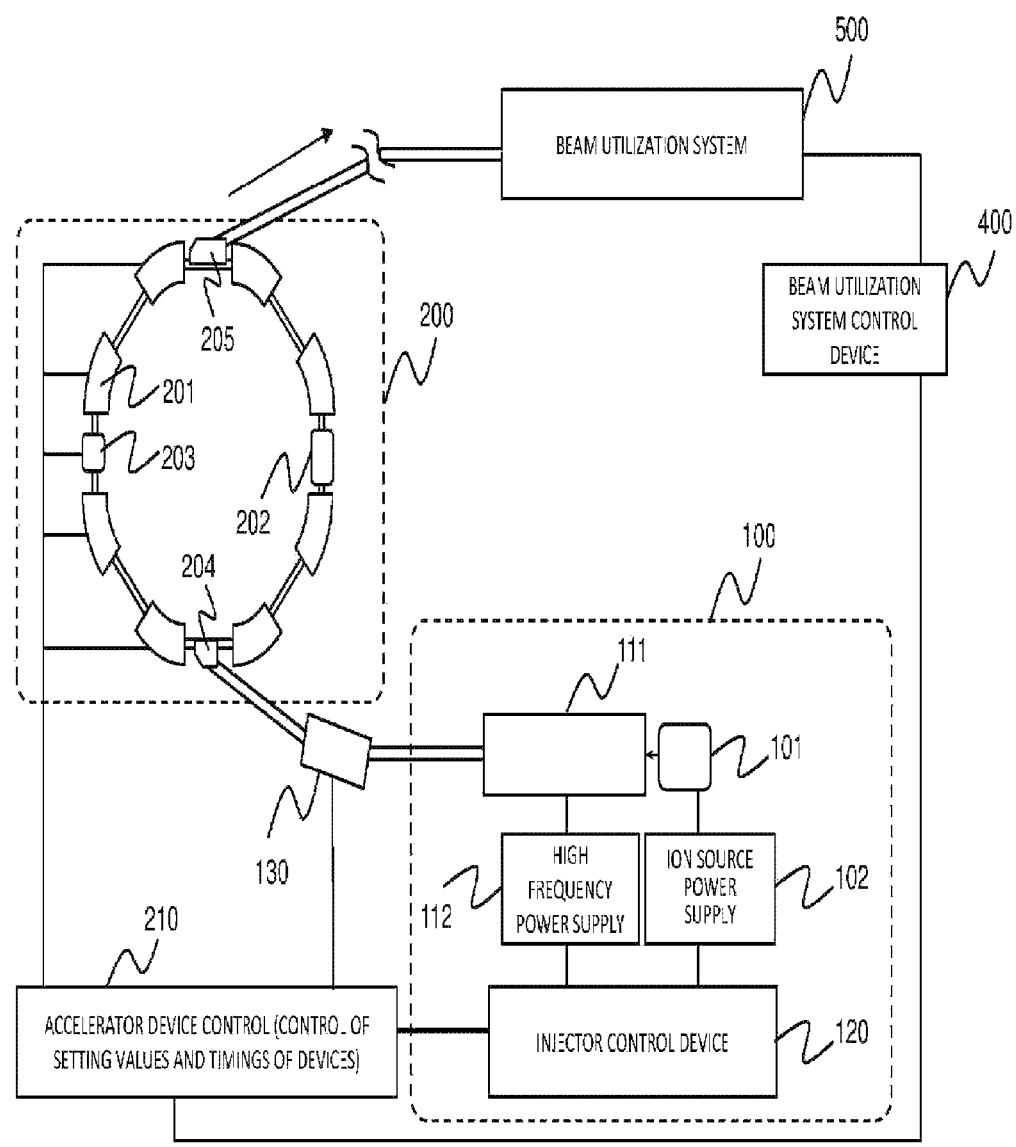
FIG. 1 is a schematic diagram illustrating an overall configuration of a charged particle beam irradiation apparatus according to a first embodiment of the present invention.

FIG. 1 is a schematic diagram illustrating an overall configuration of a charged particle beam irradiation apparatus equipped with a charged particle beam generation apparatus according to a first embodiment of the present invention.

The charged particle beam irradiation apparatus according to the embodiment is configured to include an injector system 100 which generates a charged particle beam and accelerate the charged particle beam up to the energy required for injection to a synchrotron (ring-shaped circular accelerator) 200, an injection transport system 130 which transports the charged particle beam generated by the injector system 100 to the synchrotron 200, the aforementioned synchrotron 200 which accelerates the injected charged particle beam up to desired energy, a beam utilization system 500 which utilizes the charged particle beam accelerated by the synchrotron 200, an accelerator control device (control device or second control device) 210, and a beam utilization system control device (first control device) 400.

The injector system 100 is configured to include an ion source 101 which generates charged particles, a power supply 102 for the ion source, a linear accelerator 111 which accelerates the generated charged particles, a high frequency power supply 112 which generates a pulse voltage for the acceleration, and an injector control device 120.

The synchrotron 200 is configured to include a deflection electromagnet 201, a high frequency accelerating cavity 202, beam emission devices 203 and 205, an injection device 204 used for the injection, and the like.

The injector system 100 and the synchrotron 200 are controlled by the accelerator control device 210 and are operated based on a beam emitting request signal from the control device 400 of the beam utilization system 500, a next-pattern transition request signal requesting transition of an operation pattern of the synchrotron, an energy changing request signal for changing energy emitted from the synchrotron, and the like.

The injector system 100, the synchrotron 200, and the accelerator control device 210 constitutes a charged particle beam generation apparatus.

Figure 2:
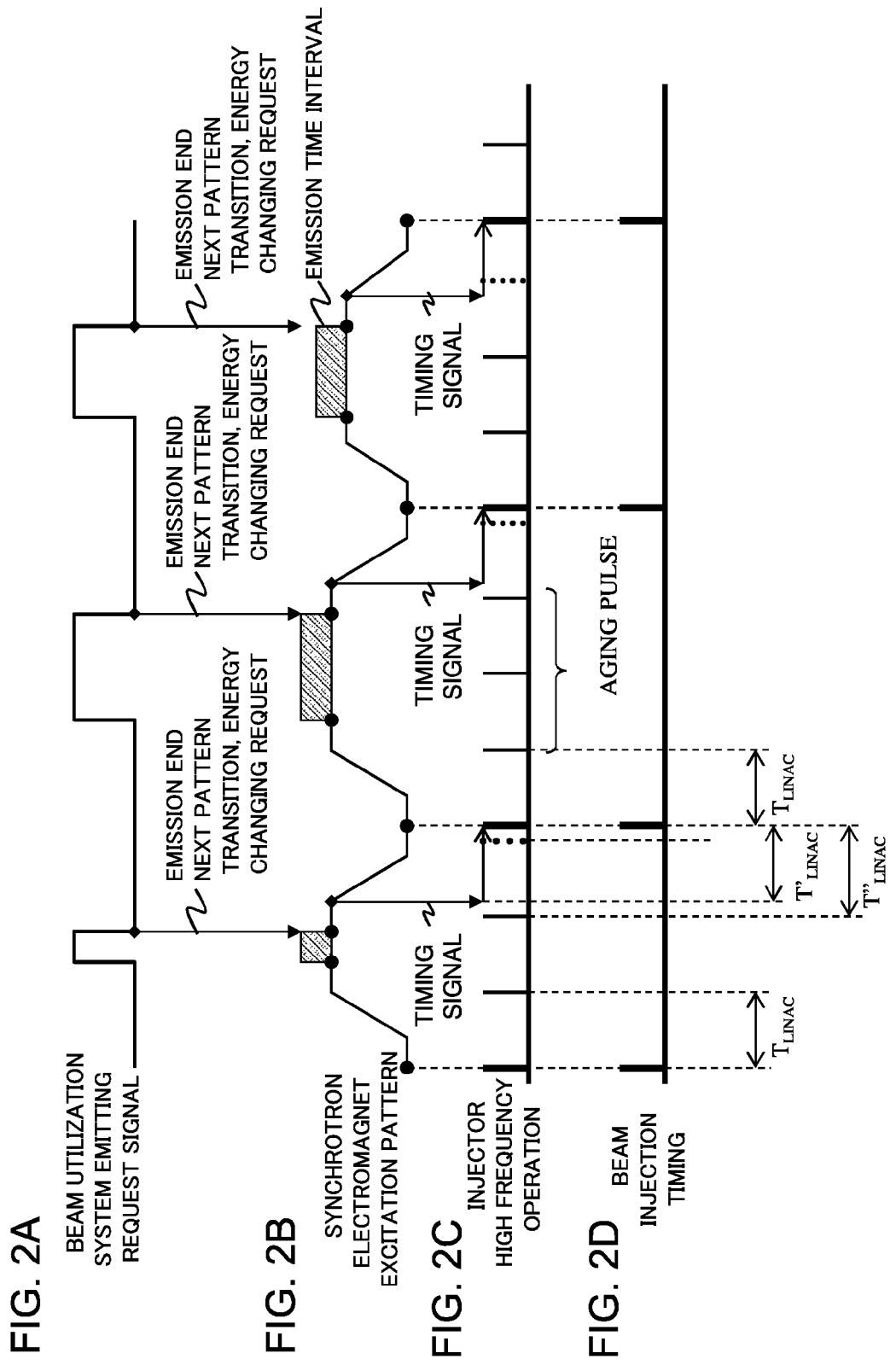
FIGS. 2A to 2D are timing charts illustrating an example of an operation of the charged particle beam irradiation apparatus according to the first embodiment of the present invention.

FIGS. 2A to 2D illustrate timing charts of typical operations. FIG. 2A illustrates a beam utilization system emitting request signal generated from the beam utilization system control device 400, which requests a charged particle beam for a condition required in the beam utilization system. FIG. 2B illustrates an excitation pattern of the deflection electromagnet 201 as a representative electromagnet excitation pattern which is an operation pattern of the synchrotron 200 and is configured with an injecting process, an accelerating process, an emitting process, and a decelerating process. The synchrotron 200 is operated by setting a time including time intervals of these processes as one operation period (one operating cycle).

Figure 3:
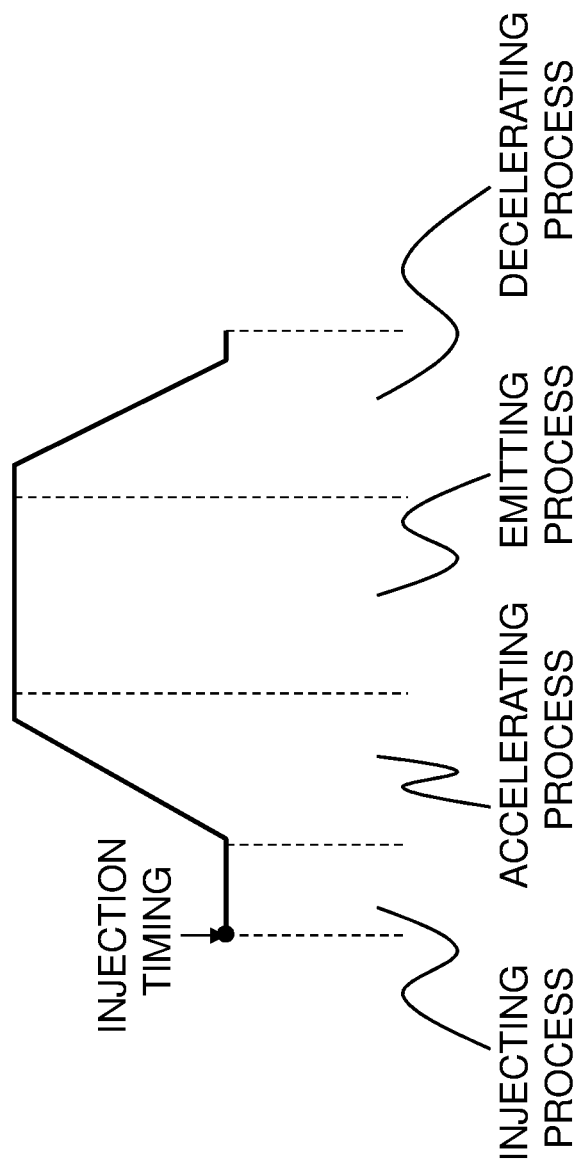
FIG. 3 is a diagram illustrating details of an operation pattern of a synchrotron of the charged particle beam irradiation apparatus according to the first embodiment of the present invention.

Details of the electromagnet excitation pattern of the synchrotron are illustrated in FIG. 3. In FIG. 3, an injection timing is a timing of injecting the charged particle beam accelerated by the linear accelerator 111 into the synchrotron 200, and the electromagnet excitation pattern and the control of high frequency acceleration or deceleration corresponding to the electromagnet excitation pattern are synchronized during the time interval from the injection timing through the injecting process and the accelerating process to the start of the emitting process and during the time interval from the end of the emitting process through the decelerating process and the end of the synchrotron pattern to the injection timing of the next cycle. The injection timing and the patterns and time intervals in the injecting process, the accelerating process, and the decelerating process are determined in advance in the production of the pattern.

On the other hand, the high frequency operation of the linear accelerator 111 is performed in a period (herein, the operation period is denoted by $T_{LINAC}$) illustrated in FIG. 2C. In FIG. 2C, "injector high frequency operation" denotes a high frequency operation period of the linear accelerator 111. In the description hereinafter, the case of "injector high frequency operation" is the same as above.

In FIGS. 2A to 2D, if the operation period of the synchrotron 200 is coincident with the injector operation period $T_{LINAC}$ or an integer multiple of $T_{LINAC}$, the injection timing of the synchrotron 200 and a timing (operating timing of the linear accelerator 111) when a beam can be supplied from the linear accelerator 111 are coincident with each other, so that the injection can be performed without problems.

However, as illustrated in FIG. 2A, in the case where the time of the emitting request signal from the beam utilization system 500 is undefined or in the case where, although the time is periodic, the operation period of the synchrotron 200 is not an integer multiple of the injector operation period $T_{LINAC}$, the injection timing required for the operation of the synchrotron 200 is not coincident with the injector operation period, but a stand-by time when the synchrotron side stands by in the injecting process occurs.

Therefore, in the embodiment, during the operation of the synchrotron 200, an after-end-of-emitting-process timing signal is generated at a timing after the end of the emitting, the high frequency operation of the linear accelerator 111 is stopped based on the after-end-of-emitting-process timing signal. Next, if a master signal (synchrotron pattern start signal) is input, the high frequency operation of the linear accelerator 111 is allowed to be started, and the injection timing of the synchrotron 200 and the timing (operating timing of the linear accelerator 111) when the beam can be supplied from the linear accelerator 111 are allowed to be coincident with each other. FIG. 2D illustrates an actual beam injection timing.

Herein, as illustrated in FIGS. 2A to 2D, a time interval from the after-end-of-emitting-process timing signal generated during the operation of the synchrotron 200 to the injection timing of the next synchrotron operation period is denoted by $T'_{LINAC}$. In addition, $T''_{LINAC}$ denotes a time interval from an operation pulse (including an aging pulse) immediately before the after-end-of-emitting-process timing signal to the next injection timing.

The generating timing of the after-end-of-emitting-process timing signal can be set by appropriately selecting a timing between the maximum period and the shortest period when a time interval from the immediately-preceding aging pulse to the next mater signal is allowable in the time interval from the end of emission to the injection timing of the next operation cycle. In addition, existing timing signals such as an emission off timing signal, a deceleration start timing signal, or a deceleration end timing signal may be used. For example, in the example illustrated in FIGS. 2A to 2D, the generating timing of the after-end-of-emitting-process timing signal is a case of a timing which is coincident with the deceleration start timing signal, and with respect to the operation period $T''_{LINAC}$ of the linear accelerator 111, the time interval from the aging pulse immediately before the after-end-of-emitting-process timing signal to the generation of the master signal is elongated.

The generating timing of the after-end-of-emitting-process timing signal is preferably set by a deceleration start timing in the case of a generation apparatus for a heavy particle beam of particles heavier than protons of carbon or the like (the deceleration start timing signal may be used as the after-end-of-emitting-process timing signal) and is preferably set by a deceleration end timing in the case of a generation apparatus for a proton beam. However, in accordance with conditions of the charged particle beam generation apparatus or the beam utilization system 500 or irradiation conditions, for example, an arbitrary timing such as spot beam amount expiration, one spill end, deceleration start, mid-deceleration, or deceleration end may be appropriately selected to be set.

In addition, "one spill" denotes one-time beam extraction time of the beam in a beam scanning method of performing scanning of a scan path several times (multi-painting).

A generating timing of the master signal (synchrotron pattern start signal) is appropriately set after a predetermined time elapses from the deceleration start timing, after a predetermined time elapses from the deceleration end, at a predetermined time before the acceleration control start timing signal, at a predetermined time before the beam utilization system emitting request signal, or the like according to a configuration of the charged particle beam generation apparatus. In addition, an existing timing signal indicating the next operation start timing may be used.

In addition, in an operation control method according to the embodiment, the operation period $T'_{LINAC}$ from the operation stop of the linear accelerator 111 to the next operation start may be longer or shorter than the original basic period $T_{LINAC}$ of the linear accelerator 111 in some cases. Hereinafter, this will be described more in detail with reference to FIGS. 4A to 4E.

In addition, as described above, if the operation period of the linear accelerator 111 is shortened, the linear accelerator 111 is stabilized, but consumption thereof is rapidly performed. In addition, if the operation period is elongated, the linear accelerator 111 is unstable, but consumption thereof is slowly performed. An operation period that is allowable in the meantime is referred to as an operation available period. The operation available period is a value depending on the configuration of the linear accelerator 111. For example, the basic period (operation available period) of the linear accelerator 111 is set to a time interval of 0.05 to 5 ec. In addition, the operation period of the synchrotron 200 is set to a time interval of 2 to 60 sec.

Figure 4:
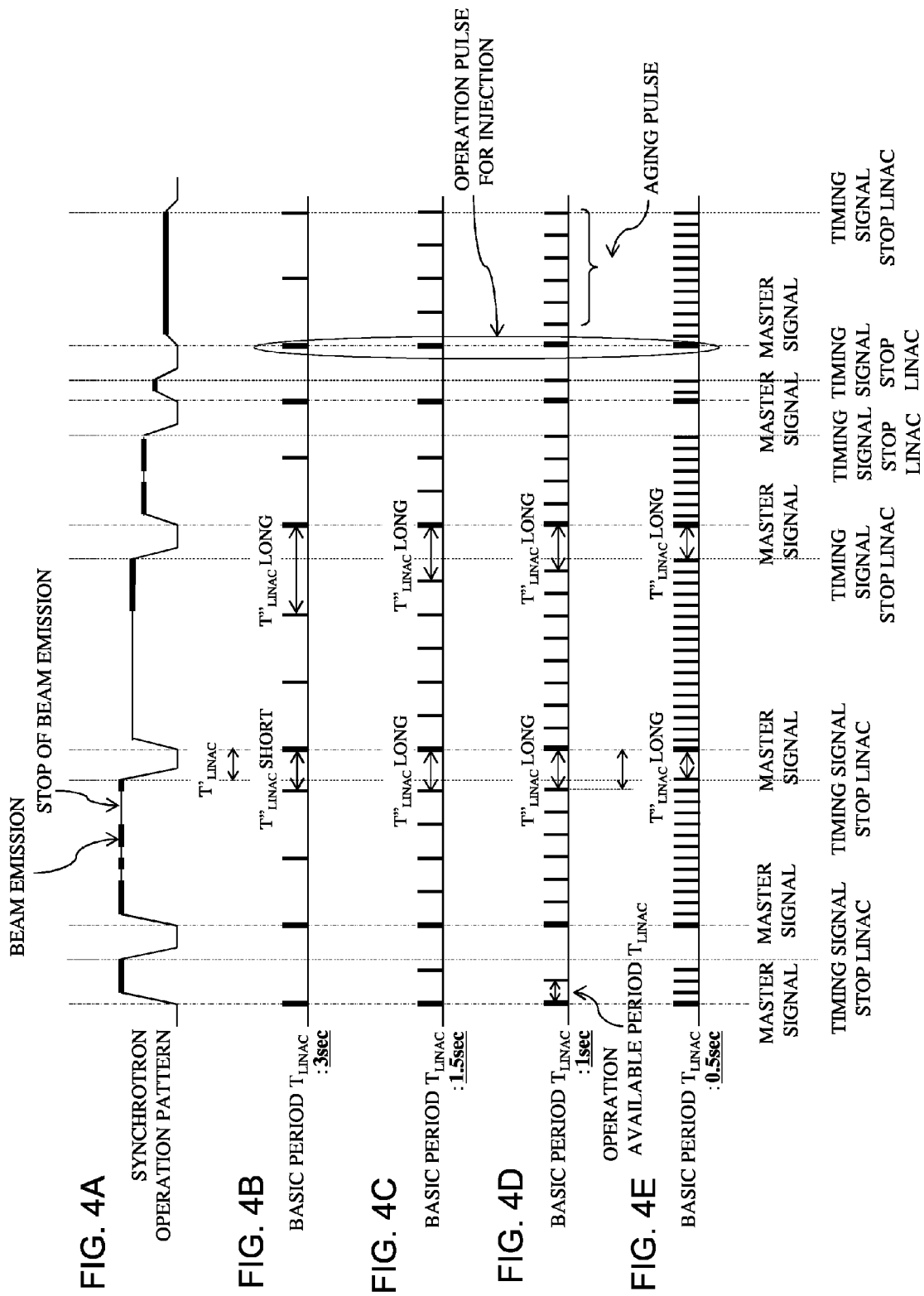
FIGS. 4A to 4E are timing charts illustrating another example of the operation of the charged particle beam irradiation apparatus according to the first embodiment of the present invention.

In some cases, as illustrated in FIG. 4A, in the mid-emission of beam from the synchrotron indicated by thick lines in FIG. 4A, for the reason such as movement of a diseased portion or the like, as illustrated in thin lines in FIG. 4A, the beam emission from the synchrotron is stopped.

In addition, with respect to the operation period $T_{LINAC}$ of the linear accelerator 111, since a capacity of the high frequency power supply or a high frequency is different according to a nuclide (for example, protons or carbons) of particles as acceleration object or energy after the acceleration, the relation between the operation period of the synchrotron 200 and the injector operation period $T_{LINAC}$ cannot be fixed.

Figure 5:
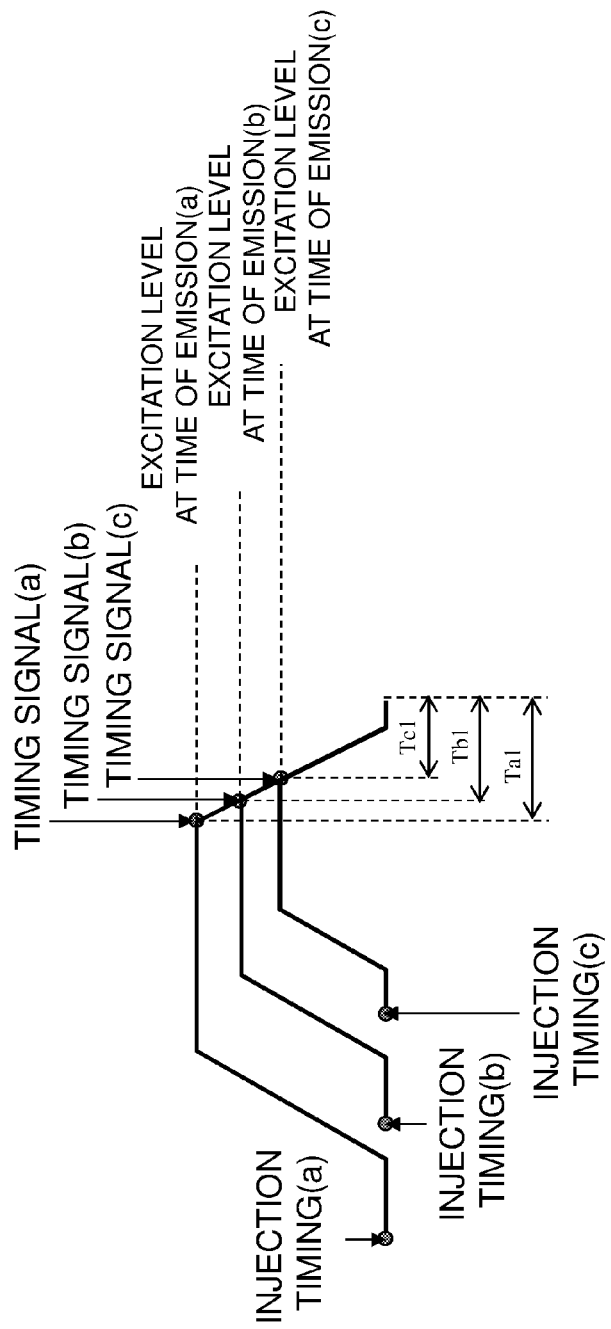
FIG. 5 is a diagram illustrating difference in the operation according to excitation level at the time of emission in the operation pattern of the synchrotron of the charged particle beam irradiation apparatus according to the first embodiment of the present invention.

For example, as illustrated in FIG. 5, since the energy at the time of emission is different, namely, the excitation level of the pattern electromagnet excitation pattern is different as illustrated in FIGS. 5 (a), (b), and (c), and in the case where a current change rate during the decelerating process is set to be constant, since the time interval of the decelerating process is different according to the energy, although the after-end-of-emitting-process timing signal is allowed to be coincident with the deceleration start timing signal, the timing which can be taken is different as indicated by a timing (a), a timing (b), and a timing (c), and the time interval T from the generation of the after-end-of-emitting-process timing signal to the injection is also different as indicated by Ta1, Tb1, and Tc1.

Similarly, since the energy at the time of emission is different, and even in the case where the current change rate during the accelerating process is set to be constant, since the time interval of the accelerating process is different according to the energy, the emitting timing is different, and the time interval from the generation of the master signal to the start of emission is also different.

For this reason, the injector operation period is not coincident with the injection timing required for the operation of the synchrotron 200, and if some measures are not performed, the stand-by time when the synchrotron side stands by in the injecting process occurs.

Even in this case, as described above, the high frequency operation of the linear accelerator 111 is allowed to be stopped based on the after-end-of-emitting-process timing signal, and if the master signal is input, the high frequency operation of the linear accelerator 111 is allowed to be started, and the injection timing of the synchrotron 200 and the timing when the beam can be supplied from the linear accelerator 111 are allowed to be coincident with each other.

In this case, as illustrated in FIG. 4B, in the case where a pulse operation basic period T of the linear accelerator 111 is set to 3 sec, $T''_{LINAC}$ is shortened or lengthened by the generating timing of the after-end-of-emitting-process timing signal. In contrast, like the case where the pulse operation basic period T of the linear accelerator 111 is set to 1.5 sec as illustrated in FIG. 4C, the case where the pulse operation basic period T of the linear accelerator 111 is set to 1 sec as illustrated in FIG. 4D, or the case where the pulse operation basic period T of the linear accelerator 111 is set to 0.5 sec as illustrated in FIG. 4E, $T''_{LINAC}$ may be merely lengthened according to the setting of the pulse operation basic period $T_{LINAC}$. In this manner, by changing the operation period $T''_{LINAC}$ from the stop of operation of the linear accelerator 111 to the start of the next operation, the beam can be supplied from the linear accelerator 111 in coincidence with the injection timing of the synchrotron 200. In addition, the change of the operation period also partially occurs, and since, in most cases, the operation can be performed in the basic operation period, the stability of the beam from the linear accelerator 111 can be maintained.

In addition, by employing the control method according to the embodiment, as illustrated in FIG. 4B, the basic period $T_{LINAC}$ is set to be long, and thus, the life cycle of the linear accelerator 111 can be elongated, and the supply responsiveness of the beam to the synchrotron for shortening the treatment time interval can be maintained.

In addition, in FIGS. 2A to 2D and FIGS. 4A to 4E, operation pulses other than the operation pulse of the linear accelerator 111 used for the injection of the beam to the synchrotron 200 generated by the master signal are pluses for aging generated for adjusting the condition of the linear accelerator 111.

In the embodiment, the accelerator control device 210 constitute a first control device which controls the emission devices 203 and 205 of the synchrotron 200 in the charged particle beam emitting process in the operation period of the synchrotron 200 so that the charged particle beam is emitted only in the time period requested from the beam utilization system. 500 (irradiation apparatus) and a second control device which generates the after-end-of-emitting-process timing signal after the end of the charged particle beam emitting process in the operation period of the synchrotron 200 by the control of the emission devices 203 and 205, stops the high frequency operation of the linear accelerator 111 based on the after-end-of-emitting-process timing signal, starts the high frequency operation of the linear accelerator 111 based on the master signal, and allows the injection timing of the synchrotron 200 and the timing when the beam can be supplied from the linear accelerator 111 to be coincident with each other.

Figure 6:
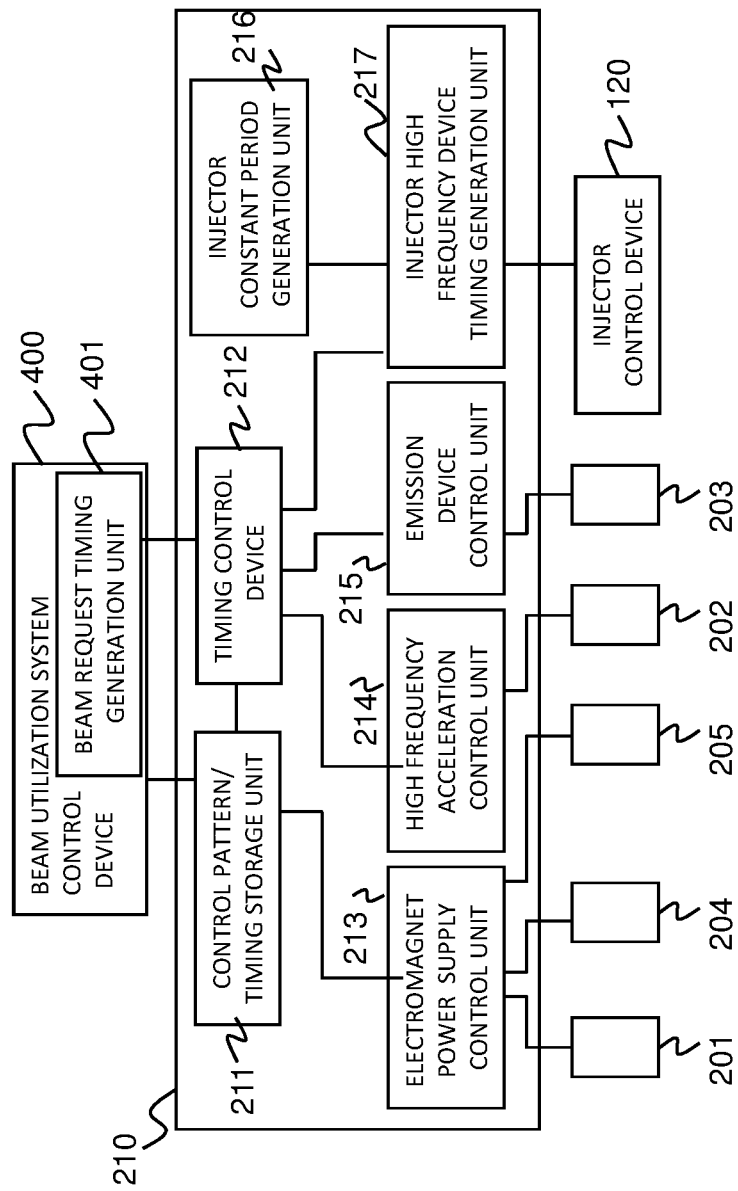
FIG. 6 is a diagram illustrating details of an accelerator control device of the charged particle beam irradiation apparatus according to the first embodiment of the present invention.

Next, details of the accelerator control device 210 for implementing the operation control method according to the embodiment illustrated in FIGS. 2A to 2D will be described with reference to FIG. 6.

The accelerator control device 210 is configured to include a control pattern/timing storage unit 211 which stores various control parameters including the electromagnet excitation pattern of the synchrotron 200 illustrated in FIG. 3 and the associated timings such as a timing of preparing acceleration or emission, a timing of deceleration, a generating timing of the master signal, a generating timing of the after-end-of-emitting-process timing signal. Herein, the generating timing of the after-end-of-emitting-process timing signal is a time point between the maximum period and the shortest period when a time interval from the immediately-preceding aging pulse to the next master signal is allowable in the time interval from the end of emission to the injection timing of the next operation cycle and is stored in association with other timing signals.

The control pattern/timing storage unit 211 is connected to an electromagnet power supply control unit 213 to control the deflection electromagnet 201, the injection device 204, and the emission device 205 which are devices inside the synchrotron 200. The timing stored in the control pattern/timing storage unit 211 is used to control other devices through a timing control device 212. Namely, the timing control device 212 controls the high frequency accelerating cavity 202 through a high frequency acceleration control unit 214 and controls the emission device 203 through an emission device control unit 215. The timing control device 212 receives an emitting request signal, a next-pattern transition signal, or an energy changing request from a beam request timing generation unit 401 installed in a beam utilization system control device 400 and operates the emission device 203 through the emission device control unit 215 to emit the beam for an emitting request.

The basic period (constant period) $T_{LINAC}$ for a high frequency device operation of the linear accelerator 111 is generated from an injector constant period generation unit 216. The basic period $T_{LINAC}$ is set in advance.

An injector high frequency device timing generation unit 217 which generates the high frequency device operating timing for the linear accelerator 111 adjusts the constant basic period from the injector constant period generation unit 216 according to the after-end-of-emitting-process timing signal or the master signal generated from the timing control device 212 and supplies the high frequency device operating timing to the injector control device 120.

The injector control device 120 repeats a start-up operation as illustrated in FIG. 2C or FIGS. 4B to 4E by synchronizing the high frequency power supply 112 illustrated in FIG. 1 with the high frequency device operating timing. However, since the beam is not required for all the times of the high frequency operation, the beam is allowed not to be accelerated, but the beam is allowed to be accelerated only at the injection timing illustrated in FIG. 2D. Namely, although the high frequency operation of the linear accelerator 111 performs operations in the operation period illustrated in FIG. 2C or FIGS. 4B to 4E, at the timing which is not coincident with the beam injection timing of FIG. 2D among the operating timings, the charged particles are controlled not to be supplied from the ion source 101, so that the linear accelerator 111 is idled (the aforementioned aging pulse), and at the time which is coincident with the beam injection timing of FIG. 2D, the charged particles generated by the ion source 101 are accelerated to be injected into the synchrotron 200. As a method of idling the linear accelerator, a means for preventing the charged particles from moving may be installed between the ion source and the linear accelerator, or the ion source may be controlled not to be operated at the timing of the aging pulse of the linear accelerator.

As described above, in the embodiment, with respect to the timing control of controlling the injecting, accelerating, emitting, and decelerating processes of the synchrotron 200, after the end of the emitting process, the linear accelerator 111 stops the repetition of the operation by the after-end-of-emitting-process timing signal generated after the end of the charged particle beam emitting process in the operation period of the synchrotron 200 to enter into the stand-by state and starts the repetition of the operation in the constant period by the master signal (synchrotron pattern start signal). In addition, the synchrotron 200 is injected with the beam from the linear accelerator 111 based on the master signal and starts a pattern of a constant period or an undefined period including the time intervals of the accelerating, emitting, and decelerating processes.

Accordingly, the injection of the charged particle beam bending portion into the synchrotron 200 can be performed at an arbitrary timing requiring the beam, and the beam injected from the linear accelerator 111 can be acquired in coincidence with the injection request timing for the synchrotron 200. Therefore, the stand-by time interval of the synchrotron 200 can be eliminated.

In addition, according to the embodiment, since the beam injected from the linear accelerator 111 can be acquired in coincidence with the injection request timing for the synchrotron 200, in the charged particle beam irradiation apparatus which uses the charged particle beam accelerated by the synchrotron 200, an irradiation time interval for a patient is shortened, and thus, the treatment time interval is reduced, so that the system can be efficiently operated.

In addition, although the injector constant period generation unit 216 or the injector high frequency device timing generation unit 217 is described as a portion of the accelerator control device 210, both or any one thereof may be a portion of the injector control device 120, and even in this case, the above-described control operation can be implemented.

In addition, the operation pattern of the synchrotron is not limited to the pattern where injection-acceleration-emission-deceleration is set as one cycle as illustrated in FIGS. 2A to 2D or FIGS. 4A to 4E and the beam is emitted in a plurality of cycles by changing energy, but so-called multi-stage emission may be used where a plurality of different energy is irradiated in one cycle like injection-acceleration-emission-acceleration-emission . . . repetition . . . -emission-deceleration or injection-acceleration-emission-acceleration-emission . . . repetition . . . -emission-deceleration-emission-deceleration-emission . . . repetition . . . -emission-deceleration.

Second Embodiment

Figure 7:
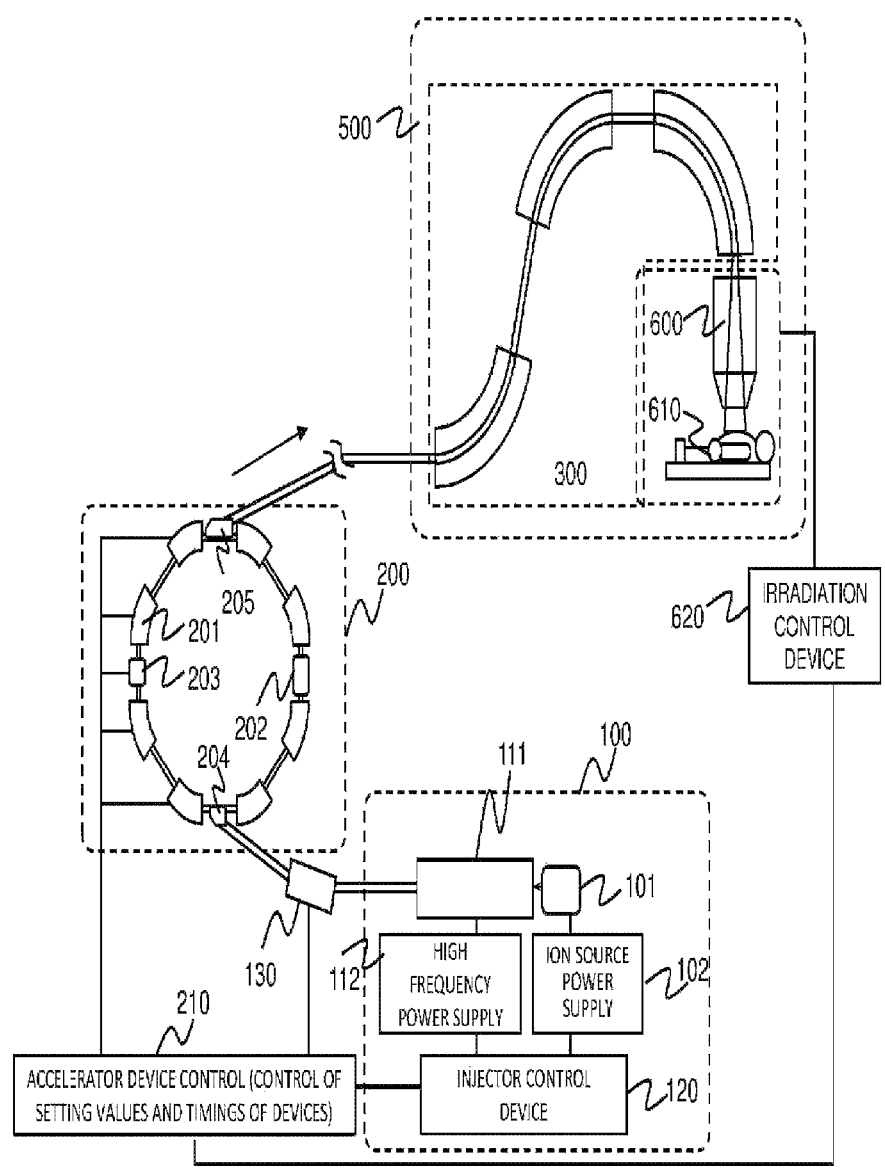
FIG. 7 is a diagram illustrating an overall configuration of a charged particle beam irradiation apparatus according to a second embodiment of the present invention.

Next, a charged particle beam irradiation system according to a second embodiment of the present invention will be described with reference to FIG. 7 and the following figures. The same components as those of the first embodiment are denoted by the same reference numerals, and the description thereof is omitted. This is the same in the following embodiments.

This embodiment is an example of a particle beam therapy system including an irradiation apparatus for implementing a treatment method of irradiating a diseased portion of a patient of a cancer or the like with a charged particle beam (ion beam) of protons, carbon ions, or the like as the beam utilization system 500 according to the first embodiment.

In the embodiment, the charged particles acquired from the synchrotron 200 are transported to an irradiation apparatus 600 through the beam transport system 300. The irradiation apparatus 600 will be described with reference to FIG. 8.

Figure 8:
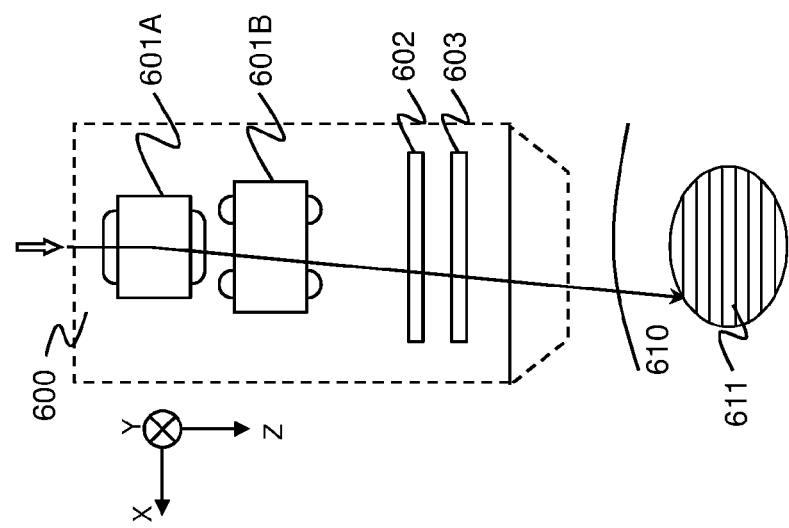
FIG. 8 is a diagram illustrating a configuration of an irradiation apparatus of the charged particle beam irradiation apparatus according to the second embodiment of the present invention.

In FIG. 8, the irradiation apparatus 600 is configured to include an X-direction scan electromagnet 601A and a Y-direction scan electromagnet 601B which scan the charged particle beam guided to the beam transport system 300 in the horizontal (X direction in the figure) and vertical (Y direction in the figure) directions in order to match with a shape of a diseased portion 611 of a patient 610. The charged particle beam deflected by the scan electromagnets 601A and 601B pass through a beam position measuring device 602 and an irradiation beam amount measuring device 603 to be irradiated on the diseased portion 611. The beam position measuring device 602 measures a position and a width (magnification) of the charged particle beam, and the irradiation beam amount measuring device 603 measures an irradiation amount of the charged particle beam.

Figure 9:
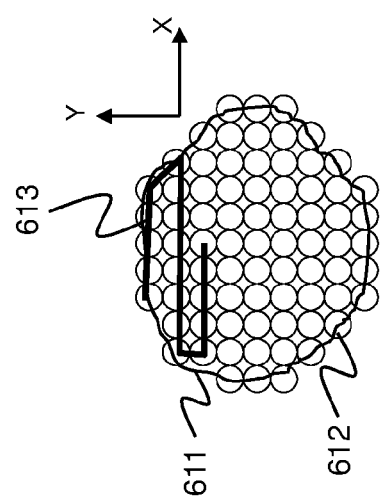
FIG. 9 is a diagram illustrating a beam amount section and a beam scan path set in a specific layer in a depth direction of a diseased portion as an irradiation object in the charged particle beam irradiation apparatus according to the second embodiment of the present invention.

Herein, the irradiation according to a beam scanning method will be described with reference to FIG. 8 and FIG. 9. FIG. 9 is an explanatory diagram as the diseased portion 611 is viewed from an upstream side of the charged particle beam.

As illustrated in FIG. 8, with respect to the diseased portion 611 of the patient 610, the shape of the diseased portion is three-dimensionally divided into a plurality of layers in the depth direction (Z direction in the figure), and as illustrated in FIG. 9, each layer is two-dimensionally divided to set a plurality of beam amount sections 612 (hereinafter, referred as irradiation spots). The depth direction corresponds to a reaching depth of the charged particle beam, and each layer is selectively irradiated by changing the energy of the charged particle beam emitted from the synchrotron 200. In each layer, as illustrated in FIG. 9, the charged particle beam is two-dimensionally scanned by the scan electromagnets 601A and 601B, for example, along a path 613, so that predetermined beam amount is applied to each irradiation spot. The amount of the charged particle beam irradiated on each irradiation spot is measured by the irradiation beam amount measuring device 603, and the position and magnification are measured by the beam position measuring device 602.

In addition, the synchrotron operation pattern of FIG. 4A is controlled so that the energy of the emitted beam is in a high state at the left of the figure and the energy is decreased as it goes to the right. Like the embodiment, in the case where the object of the utilization of the beam utilization system 500 is the irradiation of the charged particle beam (ion beam) of protons, carbon ions, or the like on a diseased portion of a patient of cancer or the like, this is control for irradiating the beam in the order from the deepest layer by matching a Bragg peak of the beam with a predetermined scan layer of a tumor. In this case, in the decelerating process after the stop of the beam emission, the synchrotron performs an operation for resetting a history of the electromagnet, and as the energy of the beam emitted immediately-precedingly is increased, the reset operation is ended in a short time. For this reason, as the immediately-preceding beam energy is increased, $T'_{LINAC}$ is shortened, and thus, the stand-by time easily occurs in a typical control, so that the effect of the application of the control according to the embodiment becomes large. In addition, if an apparatus configuration is employed where $T'_{LINAC}$ of the case where the energy of the irradiating beam is in maximum is larger than the shortest operation available period for the linear accelerator, the above-described effect according to the control method of the embodiment can be greatly obtained.

In the irradiation method according to the embodiment, the case where a next pattern transition request for the synchrotron 200 is generated corresponds to the case where the charged particles accumulated in the synchrotron 200 during the irradiation on the spots in the layer illustrated in FIG. 9 are exhausted or the case where the irradiation available time interval per unit cycle by the synchrotron 200 is exhausted. In this, the emission is stopped in the cycle, and thus, the next pattern transition timing may be undefined.

In addition, in the case where all the spots in the layer illustrated in FIG. 9 are completely irradiated, the depth direction (Z direction) indicated by 611 of FIG. 8 needs to be changed, and the energy emitted from the synchrotron 200 is changed. In this case, since the irradiation time interval for the inner portion of the layer is different according to the shape of the diseased portion 611, the emission end timing in the operating cycle of the synchrotron may become undefined.

In this manner, in the irradiation apparatus 600 according to the embodiment, since the operation period and the emission timing of the synchrotron 200 are undefined, in the case where the period of the high frequency operation of the linear accelerator 111 is fixed, there is a possibility that the charged particle beam cannot be injected at a desired injection timing of the synchrotron 200 and the irradiation time interval is increased.

Therefore, in the embodiment, in the case where the charged particles accumulated in the synchrotron 200 during the irradiation of the spots in the layer illustrated in FIG. 9 are exhausted or the case where the irradiation available time interval per unit cycle by the synchrotron 200 is exhausted, the accelerator control device 210 generates the next-pattern transition request signal of requesting the transition of the operation pattern of the synchrotron 200 and outputs the next-pattern transition request signal (first control device).

In addition, in the case where all the spots in the layer illustrated in FIG. 9 are completely irradiated, an irradiation control device 620 outputs an energy changing request signal of requesting the changing of the energy emitted from the synchrotron 200 (first control device).

When any one of these signals is input, the accelerator control device 210 performs the operation method according to the present invention illustrated in FIGS. 2A to 2D or FIGS. 4A to 4E. Namely, the high frequency operation of the linear accelerator 111 is allowed to be stopped based on the after-end-of-emitting-process timing signal, the high frequency operation of the linear accelerator 111 is allowed to be started based on the master signal, and the injection timing of the synchrotron 200 and the timing when the beam can be supplied from the linear accelerator 111 are allowed to be coincident with each other (control device, second control device).

Accordingly, in the embodiment, almost similarly to the above-described first embodiment, the injection timing can be set to be a desired timing, and thus the irradiation time interval is not increased, and the treatment time interval can be reduced, so that the particle beam therapy system capable of efficiently operating the system can be implemented.

In addition, the beam scanning method in the charged particle beam irradiation method is not limited to so-called spot canning irradiation where the irradiation spot is set, but other scanning methods such as raster scanning, zigzag scanning, helical scanning, line scanning, and single-circle scanning may be used. In addition, the charged particle beam irradiation method is not limited to the beam scanning method, but the present invention may be applied to a system employing a scattering method such as a layer stacking irradiation method.

Third Embodiment

Next, a charged particle beam irradiation system according to a third embodiment of the present invention will be described with reference to FIG. 10 and the following figures.

The embodiment is configured to include an irradiation apparatus for implementing a treatment method of irradiating a diseased portion of a patient of a cancer or the like with a charged particle beam (ion beam) such as protons, carbon ions, as the beam utilization system 500 according to the first embodiment and a device for detecting movement of the diseased portion associated with breathing of the patient or other movements.

In the embodiment, the charged particles acquired from the synchrotron 200 are transported to an irradiation apparatus 700 through the beam transport system 300. The irradiation apparatus 700 will be described with reference to FIG. 10.

Figure 10:
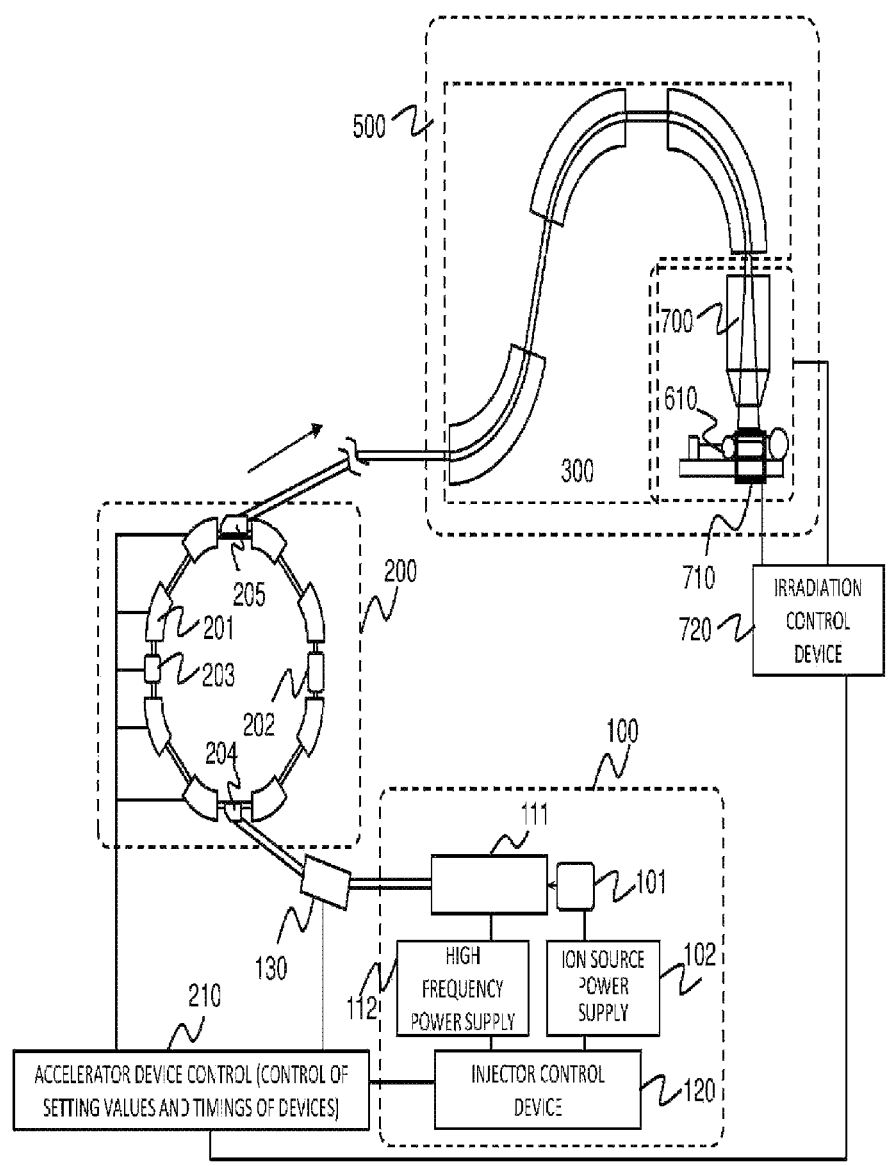
FIG. 10 is a diagram illustrating an overall configuration of a charged particle beam irradiation apparatus according to a third embodiment of the present invention.

In FIG. 10, as an irradiation field forming method of the irradiation apparatus 700, an arbitrary irradiation field forming method such as a scattering method using scattering of a charged particle beam or the above-described beam scanning method may be used. As the scattering method, for example, layer stacking irradiation may be used where the diseased portion is divided into layers, an irradiation amount for each layer is defined, if the irradiation for a layer is expired, the irradiation for the next layer is performed, and the irradiation is performed by matching multi-leaf collimator aperture with the irradiation field shape of each layer. As the beam scanning method, beside the spot scanning method illustrated in the second embodiment, there are other scanning methods such as raster scanning, zigzag scanning, helical scanning, line scanning, and single-circle scanning.

In the embodiment, as illustrated in FIG. 10, a movement detection device 710 for the diseased portion of the patient 610 is installed. In order to implement highly-accurate irradiation for the diseased portion, a method of detecting the movement of the diseased portion and performing only in the case where the movement mount is within a desired range is proposed. For example, as the movement detection device 710, a method of monitoring movement of a body surface to detect movement associated with breathing, a method of monitoring flow of exhalation and inhalation associated with the breathing of a patient by using the mouth of the patient, a method of directly monitoring a position of the diseased portion or a marker indicating the diseased portion by using an X-ray fluoroscopic image, and the like are considered.

A relation between the detection of the movement of the diseased portion and the beam irradiation will be described with reference to FIGS. 11A and 11B. FIG. 11A illustrates a signal obtained by detecting the movement of the diseased portion, and a threshold value for determining whether or not the diseased portion is located at a desired position or within a range from the desired position is set in the signal. Only in the case where a diseased portion position detection signal is in the threshold value, the beam is irradiated. In this case, the irradiation available timing of the irradiation apparatus 700 according to the embodiment is indicated in a signal illustrated in FIG. 11B, and the signal is caused by the movement associated with the movement of the patient, and thus, the timing may be undefined.

In this manner, in the irradiation apparatus 700 according to the embodiment, since the operation period and the emitting timing of the synchrotron 200 become undefined, in the case where the period of the high frequency operation of the linear accelerator 111 is fixed, there is a possibility that the charged particle beam cannot be injected at a desired injection timing of the synchrotron 200 and the irradiation time interval is increased.

Therefore, in the embodiment, the irradiation available time interval per unit cycle by the synchrotron 200 is exhausted, the next-pattern transition request signal of requesting the transition of the operation period of the synchrotron 200 is generated to be output (first control device).

The accelerator control device 210 receives the signal and performs the operation method according to the present invention illustrated in FIGS. 2A to 2D or FIGS. 4A to 4E. Namely, the high frequency operation of the linear accelerator 111 is allowed to be stopped based on the after-end-of-emitting-process timing signal, the high frequency operation of the linear accelerator 111 is allowed to be started based on the master signal, and the injection timing of the synchrotron 200 and the timing when the beam can be supplied from the linear accelerator 111 are allowed to be coincident with each other (control device, second control device).

Accordingly, in the embodiment, almost similarly to the above-described first embodiment, the injection timing can be set to be a desired timing, and thus the irradiation time interval is not increased, and the treatment time interval can be reduced, so that it is possible to obtain the effect in that the system can be efficiently operated.

Others

In addition, the present invention is not limited the above-described embodiments, but various modification examples can be included. The above-described embodiments are described for the better understanding of the present invention, but the present invention is not limited to the embodiments where all the configurations described above are not required. The present invention may be applied to a system of performing operations where the operation period of a ring-shaped circular accelerator can be changed regardless of the charged particle beam emission method or the charged particle beam irradiation method.

In addition, a portion of the configurations of an embodiment may be transferred to a configuration of another embodiment, and a configuration of an embodiment may be added to a configuration of another embodiment. In addition, with respect to a portion of configurations of each embodiment, another configuration may be added, removed, or replaced.

REFERENCE SIGNS LIST 100 injector system
101 ion source 102 ion source power supply
111 linear accelerator
112 high frequency power supply for injector
120 injector control device
130 injection transport system
200 synchrotron
201 deflection electromagnet
202 high frequency accelerating cavity
203 beam emission device
204 injection device
205 beam emission device
210 accelerator control device (control device, first control device, second control device)
211 control pattern/timing storage unit
212 timing control device
213 electromagnet power supply control unit
214 high frequency acceleration control unit
215 emission device control unit
216 injector constant period generation unit
217 injector high frequency device timing generation unit
300 beam transport system
400 beam utilization system control device (first control device)
401 beam request timing generation unit
500 beam utilization system
600 irradiation apparatus
601A, 601B scan electromagnet
602 beam position measuring device
603 irradiation beam amount measuring device
610 patient
611 diseased portion
612 beam amount section (irradiation spot)
613 irradiation path
620 irradiation control device (first control device)
700 control device
710 diseased portion movement detection device
720 irradiation control device (first control device)

The invention claimed is:

1. A charged particle beam generation apparatus comprising:
   a linear accelerator which is operated in a predetermined operation period and accelerates charged particles emitted from an ion source to emit a charged particle beam;
   a circular accelerator which is operated in an operation period including time intervals of injecting, accelerating, emitting, and decelerating processes for the charged particle beam, further accelerates and emits the charged particle beam accelerated in the linear accelerator, the charged particle beam being injected in a predefined timing; and
   a control device which, after an end of the charged particle beam emitting process in the operation period of the circular accelerator, generates an after-end-of-emitting-process timing signal, stops the linear accelerator based on the after-end-of-emitting-process timing signal, generates a synchrotron pattern start signal indicating a next operation start timing, and starts a periodic operation of the linear accelerator based on the synchrotron pattern start signal.

2. The charged particle beam generation apparatus according to claim 1, wherein
   the control device sets the after-end-of-emitting-process timing signal so as to be any timing of emission end, deceleration start, mid-deceleration, and deceleration end for the charged particle beam.

3. The charged particle beam generation apparatus according to claim 1, wherein the control device includes:
   a storage device which stores various timings associated with an operation pattern including processes of injection, acceleration, emission, and deceleration for the charged particle beam of the circular accelerator, a timing of the synchrotron pattern start signal, and a timing of the after-end-of-emitting-process timing signal;
   a timing control unit which receives an update request for the operation pattern and timing information stored in the storage unit;
   a constant period generation unit which generates an operation basic period of the linear accelerator; and
   a timing generation unit which stops the operation basic period from the constant period generation unit according to the timing of the after-end-of-emitting-process timing signal from the timing control unit, starts according to the timing of the synchrotron pattern start signal, and generates an operating timing of the linear accelerator.

4. The charged particle beam generation apparatus according to claim 1, wherein
   an operation period $T'_{LINAC}$ from stop of the operation of the linear accelerator to start of the next operation in the case where energy of the beam emitted from the ring-shaped circular accelerator is in maximum is larger than the shortest operation available period for the linear accelerator.

5. A charged particle beam irradiation apparatus comprising:
   the charged particle beam generation apparatus according to claim 1;
   an irradiation apparatus which uses the charged particle beam emitted from the circular accelerator;
   a first control device which controls an emission device of the circular accelerator in the charged particle beam emitting process in the operation period of the circular accelerator so as to emit the charged particle beam only in the time interval requested by the irradiation apparatus; and
   a second control device which generates an after-end-of-emitting-process timing signal after the end of the charged particle beam emitting process in the operation period of the circular accelerator by control of the emission device, stops the linear accelerator based on the after-end-of-emitting-process timing signal, generates a synchrotron pattern start signal indicating a next operation start timing, and starts an operation of a predetermined operation period of the linear accelerator and an operation of the linear accelerator based on the synchrotron pattern start signal.

6. A charged particle beam irradiation apparatus comprising:
   the charged particle beam generation apparatus according to claim 1;
   an irradiation apparatus which includes a scan electromagnet deflecting the charged particle beam emitted from the circular accelerator and performing scanning and irradiates an irradiation object with the charged particle beam passing through the scan electromagnet;
   a first control device which scans the charged particle beam by controlling excitation current of the scan electromagnet with respect to one of a plurality of layers obtained by dividing the irradiation object for the charged particle beam in a depth direction and outputs an energy changing request for requesting changing of the energy of the charged particle beam emitted from the circular accelerator in order to scan the charged particle beam with respect to another layer after the end of scanning of the charged particle beam with respect to the one layer; and a second control device which, at the time of transitioning the operation period of the circular accelerator to a next operation period according to the energy changing request, after the end of the charged particle beam emitting process in the operation period of the circular accelerator, generates an after-end-of-emitting-process timing signal, stops the linear accelerator based on the after-end-of-emitting-process timing signal, generates a synchrotron pattern start signal indicating a next operation start timing, and starts an operation in a predetermined operation period of the linear accelerator and an operation of the linear accelerator based on the synchrotron pattern start signal.

7. A charged particle beam irradiation apparatus comprising:

the charged particle beam generation apparatus according to claim 1;

an irradiation apparatus which includes a scan electromagnet deflecting the charged particle beam emitted from the circular accelerator and performing scanning and irradiates an irradiation object with the charged particle beam passing through the scan electromagnet;

a first control device which scans the charged particle beam by controlling excitation current of the scan electromagnet with respect to the irradiation object for the charged particle beam and, in the case where the charged particle beam accumulated in the circular accelerator is exhausted during the scanning of the charged particle beam or the case where an irradiation available time interval per unit operation period in the circular accelerator during the scanning of the charged particle beam is exhausted, stops the emitting process in the operation period of the circular accelerator and outputs an operation pattern transition request for requesting transition to an operation pattern in a next operation period; and a second control device which, at the time of transitioning the operation period of the circular accelerator to the next operation period according to the operation pattern transition request, after the end of the charged particle beam emitting process in the operation period of the circular accelerator, generates an after-end-of-emitting-process timing signal, stops the linear accelerator based on the after-end-of-emitting-process timing signal, generates a synchrotron pattern start signal indicating a next operation start timing, and starts an operation in a predetermined operation period of the linear accelerator and an operation of the linear accelerator based on the synchrotron pattern start signal.

8. A charged particle beam irradiation apparatus comprising:

the charged particle beam generation apparatus according to claim 1;

an irradiation apparatus which irradiates an irradiation object with the charged particle beam emitted from the circular accelerator to match the charged particle beam with a shape of the irradiation object by temporally or spatially shaping;

a first control device which sets a timing in a time range of an irradiation available time interval for the irradiation object from a signal obtained by detecting movement of the irradiation object and output a beam request for requesting beam emission only in the time interval of the time range;

a second control device which at the time of transitioning the operation period of the circular accelerator to a next operation period according to the beam request, after the end of the charged particle beam emitting process in the operation period of the circular accelerator, generates an after-end-of-emitting-process timing signal, stops the linear accelerator based on the after-end-of-emitting-process timing signal, generates a synchrotron pattern start signal indicating a next operation start timing, and starts an operation in a predetermined operation period of the linear accelerator and an operation of the linear accelerator based on the synchrotron pattern start signal.

9. A particle beam therapy system irradiating a diseased portion of a patient with a charged particle beam, comprising:

a linear accelerator which is operated in a predetermined operation period and accelerates charged particles emitted from an ion source;

a circular accelerator which is operated in an operation period including time intervals of injecting, accelerating, emitting, and decelerating processes for the charged particle beam, injects the charged particle beam accelerated by the linear accelerator in a predefined timing and accelerates the charged particle beam to emit the charged particle beam;

a beam transport device which transports the charged particle beam emitted from the circular accelerator to an irradiation point;

an irradiation apparatus which irradiates the diseased portion with the charged particle beam transported by the beam transport system;

a control unit which controls the circular accelerator, the beam transport device, and the irradiation apparatus;

a linear accelerator control device which, after an end of the charged particle beam emitting process in the operation period of the circular accelerator, generates an after-end-of-emitting-process timing signal, stops the linear accelerator based on the after-end-of-emitting-process timing signal, generates a synchrotron pattern start signal indicating a next operation start timing, and starts an operation in a predetermined operation period of the linear accelerator and an operation of the linear accelerator based on the synchrotron pattern start signal.

10. A method of operating a charged particle beam generation apparatus comprising providing the charged particle beam generation apparatus including a linear accelerator which is operated in a predetermined operation period and accelerates charged particles emitted from an ion source to emit a charged particle beam and a circular accelerator which is operated in an operation period including time intervals of injecting, accelerating, emitting, and decelerating processes for the charged particle beam, injects the charged particle beam accelerated by the linear accelerator in a predefined timing and accelerates the charged particle beam to emit the charged particle beam, after an end of the charged particle beam emitting process in an operation period of the circular accelerator, generating an after-end-of-emitting-process timing signal, stopping the linear accelerator based on the after-end-of-emitting-process timing signal, generating a synchrotron pattern start signal indicating a next operation start timing, and starting an operation in a predetermined operation period of the linear accelerator and an operation of the linear accelerator based on the synchrotron pattern start signal.

11. The method according to claim 10, wherein
the after-end-of-emitting-process timing signal is set so as
to be any timing before an end of a synchrotron pattern
such as emission end, deceleration start, mid-deceleration, and deceleration end for the charged particle
beam.

* * * * *